United States Patent [19]

Kleinschroth et al.

[11] Patent Number: 4,720,499

[45] Date of Patent: Jan. 19, 1988

[54] TREATING BLOOD VESSEL DISEASES WITH PYRIDO[4,3-B][1,6]NAPHTHYRIDINE-DERIVATIVES

[75] Inventors: Jürgen Kleinschroth, Denzlingen; Karl Mannhardt, Elzach-Oberprechtal; Bernd Wagner; Günter Weinheimer, both of Denzlingen, all of Fed. Rep. of Germany

[73] Assignee: Godecke Aktiengesellschaft, Berlin, Fed. Rep. of Germany

[21] Appl. No.: 23,585

[22] Filed: Mar. 9, 1987

[30] Foreign Application Priority Data

Mar. 22, 1986 [DE] Fed. Rep. of Germany ....... 3609795

[51] Int. Cl.$^4$ ................... A61K 31/44; C07D 471/14
[52] U.S. Cl. ....................................... 514/293; 546/82
[58] Field of Search ........................... 546/82; 514/293

[56] References Cited

U.S. PATENT DOCUMENTS 4,202,981  5/1980  Hammond et al. .................. 546/82

*Primary Examiner*—Richard A. Schwartz
*Attorney, Agent, or Firm*—Elizabeth M. Anderson

[57] ABSTRACT

The present invention provides a unique series of pyrido[4,3-b][1,6]naphthyridine derivatives. The compounds are calcium antagonists and are useful for blood vessel diseases. This invention also covers processes for preparing the compounds, pharmaceutical compositions containing them, and methods for using them.

14 Claims, No Drawings

TREATING BLOOD VESSEL DISEASES WITH PYRIDO[4,3-B][1,6]NAPHTHYRIDINE-DERIVATIVES

BACKGROUND OF THE INVENTION

The present invention is concerned with new pyrido[4,3-b][1,6]naphthyridine derivatives, with processes for the preparation thereof and with pharmaceutical compositions containing them.

SUMMARY AND DETAILED DESCRIPTION

The new pyrido[4,3-b][1,6]naphthyridine derivatives of the present invention are compounds of the formula

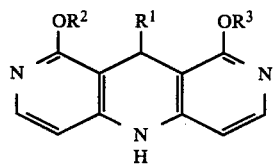
(I)

and the tautomers thereof of the formulae

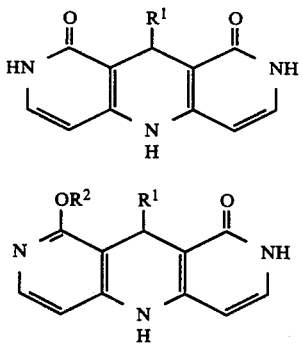

wherein $R^1$ is an unsubstituted or substituted aromatic or heteroaromatic ring or a condensed aromatic or heteroaromatic ring system and $R^2$ and $R^3$, which can be the same or different, are hydrogen atoms or straight-chained or branched alkyl radicals containing from 1 to 4 carbon atoms; and the pharmacologically acceptable salts thereof.

Preferred pyrido[4,3-b][1,6]naphthyridine derivatives of formulae (I), (Ia) and (Ib) are compounds in which $R^1$ is an unsubstituted phenyl radical or a phenyl radical preferably substituted in the 2- or 3-position by halogen, methoxy, difluoromethoxy, cyano, methylthio or trifluoromethyl or a phenyl radical disubstituted preferably in the 2,3-position by methylenedioxy or in the 2,3- or 2,6-position by trifluoromethyl or halogen atoms, which can be the same or different, or is a naphthyl or 2,1,3-benzoxadiazolyl radical and $R^2$ and $R^3$, which can be the same or different, are hydrogen atoms or methyl, ethyl, n-propyl, isopropyl, n-butyl or sec-butyl radicals.

Especially preferred pyrido[4,3-b][1,6]naphthyridine derivatives of general formulae (I), (Ia) and (Ib) are compounds in which $R^1$ is an unsubstituted phenyl radical or a phenyl radical substituted preferably in the 2- or 3-position by a cyano, nitro or trifluoromethyl radical and $R^2$ and $R^3$, which can be the same or different, are hydrogen atoms or methyl, ethyl, n-propyl, isopropyl, n-butyl or sec-butyl radicals.

The present invention also provides a process for the preparation of pyrido[4,3-b][1,6]naphthyridine derivatives of formulae (I), (Ia) and (Ib), wherein either (a) a 1,4-dihydropyridine of the formula

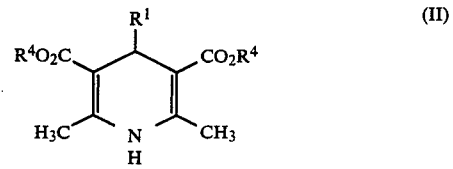
(II)

in which $R^1$ has the same meaning as above and $R^4$ is a methyl or ethyl radical, is reacted in the presence of a base with at least 2 equivalents of s-triazine and the compound of general formula (Ia) initially obtained in this way is 0-alkylated in known manner, preferably to give a symmetrically substituted compound of formula (I); or (b) a 1,6-naphthyridine derivative of the formula

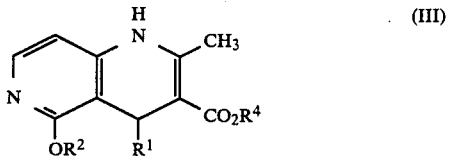
(III)

in which $R^1$, $R^2$ and $R^4$ have the same meanings as above, is reacted in the presence of a base with at least 1 equivalent of s-triazine and the compound of formula (Ib) obtained in this way is 0-alkylated in known manner, preferably to give an asymmetrically substituted compound of general formula (I).

The dihydropyridines of formula (II) used for process (a) are known (Chem. Rev., 82, 223, 1982) or they can be prepared in an analogous manner.

The 1,6-naphthyridines of formula (II) used for process (b) are described in German Pat. No. 34 31 303 or are obtainable in an analogous manner.

For carrying out reactions (a) and (b), the 1,4-dihydropyridine or 1,6-naphthyridine derivative is reacted with s-triazine in an inert organic solvent in the presence of a strong base, for example an alkali metal alcoholate or sodium hydride, at a temperature of from 50° to 160° C., and preferably of from 100° to 150° C. As solvents, there are hereby especially preferred polar solvents, such as dimethyl sulphoxide, dimethylformamide, ethylene glycol dimethyl ether or lower alcohols, such as ethanol.

The preparation of the pyrido[4,3-b][1,6]naphthyridines of formulae (I) and (Ib) takes place, according to the present invention, according to the processes usual for the 0-alkylation of lactams which are described in the literature (Adv. Heterocyclic Chem., 12, 185–212, 1970). Examples of alkylation agents which can be used include alkyl halides and alkyl sulphonates, dialkyl sulphates and trialkyloxonium salts.

For the reaction with alkyl halides, the compounds of formulae (Ia) and (Ib) are used in the form of their metal salts, preferably of their alkali metal or silver salts, which are either prepared separately or are produced in situ with the help of appropriate bases, such as metal hydrides, carbonates or alkoxides, in an aprotic solvent.

As appropriate solvents, there can be used, dependent upon the alkylation agent used, practically all inert organic solvents, such as open-chained, cyclic or also aromatic hydrocarbons, for example n-pentane, n-hexane, cyclohexane, benzene or toluene, halogenated hydrocarbons, such as dichloromethane or 1,2-dichloroethane, ethers, such as diethyl ether or 1,2-dimethoxyethane, as well as dipolar aprotic solvents, such as dimethylformamide, hexamethylphosphoric acid triamide or dimethyl sulphoxide.

Depending upon the solvent used, the temperature range can be varied from −20° C. to the boiling point of the solvent used.

Because of the ambient character of the lactam anion, in the case of the alkylation there are frequently obtained mixtures of 0- and N-alkylation products, depending upon the reaction conditions and the alkylation agent used (J. Org. Chem., 32, 4040 et seq., 1967). The separation of the product mixtures obtained can be carried out by chromatographic methods and/or by crystallization.

The pyrido[4,3-b][1,6]naphthyridines of formulae (I) and (Ib) are preferably obtained by reacting the compounds of formulae (Ia) or (Ib) with trimethyl or triethyloxonium salts, especially with trimethyloxonium tetrafluoroborate, in an aprotic solvent. The preparation of the 0-isopropyl compounds, on the other hand, preferably takes place by alkylation of the alkali metal salts with isopropyl halides.

Since the compounds according to the present invention of formulae (I), (Ia) and (Ib) possess a chiral centre on C-4, they can be present either as racemic mixtures or in the form of enantiomers.

The compounds of formulae (I), (Ia) and (Ib) are highly effective calcium antagonists. Because of their blood vessel spasmolytic actions, they are especially indicated in cases of cerebral, cardiac and peripheral blood vessel diseases.

Therefore, the new pyrido[4,3-b][1,6]naphthyridines of the present invention are valuable agents for combating heart-circulation mortality.

The compounds of formulae (I), (Ia) and (Ib) according to the present invention can be administered orally or parenterally in liquid or solid form. As injection solution, it is especially preferred to use water which contains the additives usual in the case of injection solutions, such as stabilizing agents, solubilizing agents or buffers.

Additives of this kind include, for example, tartrate and citrate buffers, ethanol and complex formers (such as ethylenediamine-tetraacetic acid and the non-toxic salts thereof), as well as high molecular weight polymers (such as liquid polyethylene oxide) for viscosity regulation. Solid carrier materials include, for example, starch, lactose, mannitol, methyl cellulose, talc, highly dispersed silicic acid, high molecular weight fatty acids (such as stearic acid), gelantine, agar-agar, calcium phosphate, magnesium stearate, animal and vegetable fats and solid high molecular weight polymers (such as polyethylene glycol). Compositions suitable for oral administration can, if desired, contain additional flavoring and/or sweetening agents.

The enterally administered individual doses are in the range of from about 5 to 250 mg and preferably of from 20 to 100 mg. About 1 to 20 mg are administered parenterally.

The following examples are given for the purpose of illustrating the present invention.

EXAMPLE 1

1,2,5,8,9,10-Hexahydro-1,9-dioxo-10-(2-trifluoromethylphenyl)-pyrido[4,3-b][1,6]naphthyridine A solution of 39.7 g (0.1 mole) diethyl 1,4-dihydro-2,6-dimethyl-4-(2-trifluoromethylphenyl)-pyridine-3,5-dicarboxylate in 250 ml dimethylformamide is added dropwise, under an atmosphere of nitrogen, to a suspension of 6.0 g (0.2 mole) sodium hydride (80% in oil) in 100 ml dry dimethylformamide. After cessation of the evolution of gas, the reaction mixture is further stirred for 10 minutes at ambient temperature and subsequently 16.2 g (0.2 mole) s-triazine in 50 ml dimethylformamide are added dropwise thereto. The reaction mixture is stirred for 16 hours at 105° C. and, after cooling, evaporated in a vacuum. The residue is taken up in 200 ml ethanol and the crystals which separate out after stirring in an ice bath for several hours are filtered off. The mother liquor contains, as by-product, the ethyl (±)-1,4,5,6-tetrahydro-2-methyl-5-oxo-4-(2-trifluoromethylphenyl)-1,6-naphthyridine-3-carboxylate already described in German Pat. No. 33 27 650. The crystals are placed into an extraction column and extracted with methanol for 24 hours. After cooling, from the methanol solution there crystallize 1,2,5,8,9,10-hexahydro-1,9-dioxo-10-(2-trifluoromethylphenyl)-pyrido[4,3-b][1,6]naphthyridine in the form of pale beige crystals; mp 350° C. (dec).

EXAMPLE 2

(±)-1,2,5,10-Tetrahydro-9-isopropoxy-1-oxo-10-(2-trifluoromethylphenyl)-pyrido[4,3-b][1,6]naphthyridine A solution of 11.3 g (27 mMole) ethyl (±)-1,4-dihydro-5-isopropoxy-2-methyl-4-(2-trifluoro methylphenyl)-1,6-naphthyridine-3-carboxylate in 200 ml dimethylformamide is added dropwise, under an atmosphere of nitrogen, to a suspension of 1.0 g (33 mMole) sodium hydride (80% in oil) in 20 ml dry dimethylformamide. After cessation of the gas evolution, the reaction mixture is stirred for 10 minutes at ambient temperature and subsequently 2.5 g (31 mMole) s-triazine in 20 ml dimethylformamide are added dropwise thereto. The reaction mixture is stirred for 16 hours at 105° C. and, after cooling, evaporated in a vacuum. The residue is chromatographed on silica gel with dichloromethane/methanol (95:5 v/v) and the fraction with an Rf of 0.6 is isolated and recrystallized from ethyl acetate/ethanol (9:1 v/v). There is obtained (±)-1,2,5,10-tetrahydro-9-isopropoxy-1-oxo-10-(2-trifluoromethylphenyl)-pyrido[4,3-b][1,6]naphthyridine in the form of colorless crystals; mp 315° C.

The following compounds are obtained in an analogous manner:
(±)-1,2,5,10-tetrahydro-9-isopropoxy-1-oxo-10-phenyl-pyrido[4,3-b][1,6]naphthyridine (2.a) mp 299°–300° C., recrystallized from ethyl acetate/ethanol,
(±)-10-(2-cyanophenyl)-1,2,5,10-tetrahydro-9-isopropoxy-1-oxo-pyrido[4,3-b][1,6]naphthyridine (2.b) mp 310°–315° C., recrystallized from ethanol.

EXAMPLE 3

(±)-5,10-Dihydro-1-isopropoxy-9-methoxy-10-(2-trifluoromethylphenyl)-pyrido[4,3-b][1,6]naphthyridine 7.5 g (18.7 mMole) (±)-1,2,5,10-tetrahydro-9-isopropoxy-1-oxo-10-(2-trifluoromethylphenyl)-pyrido[4,3-b][1,6]naphthyridine (see Example 2) and 5.0 g (34 mMole) trimethyloxonium tetrafluoroborate are stirred for 24 hours at ambient temperature in 200 ml 1,2-dichloroethane under an atmosphere of nitrogen. The reaction mixture is then shaken with a saturated aqueous solution of potassium hydrogen carbonate and the organic phase is separated off, washed with water and dried over anhydrous sodium sulphate. The residue obtained after evaporation in a vacuum is chromatographed on silica gel with toluene/ethyl acetate (3:1 v/v). The fraction with the Rf of 0.2 is isolated and recrystallized from n-hexane/diisopropyl ether. There is obtained (±)-5,10-dihydro-1-isopropoxy-9-methoxy-10-(2-trifluoromethylphenyl)-pyrido[4,3-b][1,6]naphthyridine in the form of colorless crystals; mp 183°–185° C.

The following compounds are obtained in an analogous manner:

(±)-10-(2-cyanophenyl)-5,10-dihydro-1-isopropoxy-9-methoxy-pyrido[4,3-b][1,6]naphthyridine, (3.a)

(±)-5,10-dihydro-1-isopropoxy-9-methoxy-10-(3-nitrophenyl)-pyrido[4,3-b][1,6]naphthyridine, (3.b) and (±)-1-sec-butoxy-5,10-dihydro-9-methoxy-10-(2-trifluoromethylphenyl)-pyrido[4,3-b][1,6]naphthyridine (3.c).

EXAMPLE 4

5,10-Dihydro-1,9-diisopropoxy-10-(2-trifluoromethylphenyl)-pyrido[4,3-b][1,6]naphthyridine 3.6 g (10 mMole) 1,2,5,8,9,10-hexahydro-1,9-dioxo-10-(2-trifluoromethylphenyl)-pyrido[4,3-b][1,6]naphthyridine are introduced portionwise into a suspension of 0.6 g (20 mMole) sodium hydride (80% in oil) in 100 ml dry dimethylformamide. After termination of the gas evolution, the reaction mixture is stirred for 10 minutes at ambient temperature and subsequently a solution of 5.1 g (30 mMole) isopropyl iodide in 10 ml dimethylformamide is added dropwise thereto. After 48 hours, the reaction mixture is evaporated in a vacuum and the residue is chromatographed on silica gel with toluene-/ethyl acetate (3:1 v/v). The fraction with the Rf of 0.4 is isolated and recrystallized from n-hexane. There is obtained 5,10-dihydro-1,9-diisopropoxy-10-(2-trifluoromethylphenyl)-pyrido[4,3-b][1,6]naphthyridine in the form of colorless crystals; mp 196°–197° C.

We claim:

1. A compound of the formula

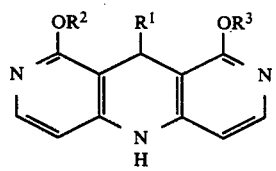

I or a tautomer thereof selected from the group consisting of

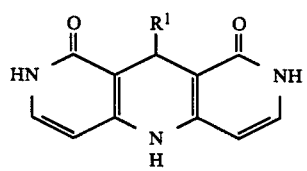

(Ia)

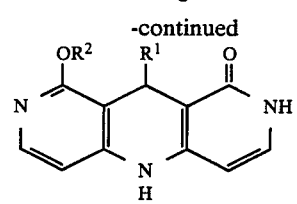

(Ib)

wherein $R^1$ is unsubstituted phenyl; phenyl substituted at the 2- or 3-position by halogen, methoxy, difluoromethoxy, cyano, methylthio or trifluoromethyl; phenyl disubstituted in the 2,3-position by methylenedioxy; phenyl disubstituted in the 2,3- or the 2,6-positions by trifluoromethyl or halogen which can be the same or different; naphthyl, or 2,1,3-benzoxadiazolyl and $R^2$ and $R^3$, which can be the same or different, are hydrogen, a straight or branched alkyl containing from one to four carbon atoms, or a pharmacologically acceptable salt thereof.

2. A compound according to claim 1 wherein $R^2$ and $R^3$ can be the same or different and are hydrogen, methyl, ethyl, n-propyl, isopropyl, n-butyl, or sec-butyl.

3. A compound of the formula

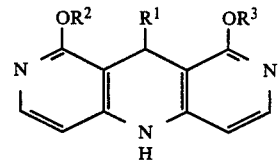

or a tautomer thereof wherein $R^1$ is unsubstituted phenyl or phenyl substituted at the 2- or 3-position by cyano, nitro, or trifluoromethyl and $R^2$ and $R^3$ can be the same or different and are hydrogen, methyl, ethyl, n-propyl, isopropyl, n-butyl, or sec-butyl.

4. A compound according to claim 1 and being 1,2,5,8,9,10-hexahydro-1,9-dioxo-10-(2-trifluoromethylphenyl)-pyrido[4,3-b][1,6]naphthyridine.

5. A compound according to claim 1 and being (±)-1,2,5,10-tetrahydro-9-isopropoxy-1-oxo-10-(2-trifluoromethylphenyl)-pyrido[4,3-b][1,6]naphthyridine.

6. A compound according to claim 1 and being (±)-5,10-dihydro-1-isopropoxy-9-methoxy-10-(2-trifluoromethylphenyl)-pyrido[4,3-b][1,6]naphthyridine.

7. A compound according to claim 1 and being 5,10-dihydro-1,9-diisopropoxy-10-(2-trifluoromethylphenyl)-pyrido[4,3-b][1,6]naphthyridine.

8. A compound according to claim 1 and being (±)-1,2,5,10-tetrahydro-9-isopropoxy-1-oxo-10-phenyl-pyrido[4,3-b][1,6]naphthyridine.

9. A compound according to claim 1 and being (±)-10-(2-cyanophenyl)-1,2,5,10-tetrahydro-9-isopropoxy-1-oxo-pyrido[4,3-b][1,6]naphthyridine.

10. A compound according to claim 1 and being (±)-10-(2-cyanophenyl)-5,10-dihydro-1-isopropoxy-9-methoxy-pyrido[4,3-b][1,6]naphthyridine.

11. A compound being (±)-5,10-dihydro-1-isopropoxy-9-methoxy-10-(3-nitrophenyl)-pyrido[4,3-b][1,6]naphthyridine.

12. A compound according to claim 1 and being (±)-1-sec.-butoxy-5,10-dihydro-9-methoxy-10-(2-trifluoromethylphenyl)-pyrido[4,3-b][1,6]-naphthyridine.

13. A vasospasmolytically effective pharmaceutical composition comprising an effective amount of a compound as defined in claim 1 in combination with a pharmaceutically acceptable carrier.

14. A method of treating blood vessel diseases in mammals which comprises administering to said mammal a pharmaceutical composition in accordance with claim 13.

* * * * *